United States Patent [19]

Halfon

[11] 4,173,229

[45] Nov. 6, 1979

[54] THERAPEUTIC ADORNMENTS UTILIZING SOLAR CELLS

[76] Inventor: Leon Halfon, 957 N. Palm Ave., Los Angeles, Calif. 90069

[21] Appl. No.: 833,503

[22] Filed: Sep. 15, 1977

[51] Int. Cl.$^2$ .............................................. A61N 1/18
[52] U.S. Cl. .................................. 128/419 R; 63/1 R
[58] Field of Search ................... 128/2.1 A, 391, 392, 128/419 R, 421, 410, 411, 380, 381, 384, 389; 63/1 R

[56] References Cited

U.S. PATENT DOCUMENTS

| 204,502 | 6/1878 | Osselin et al. | 128/389 |
|---|---|---|---|
| 526,182 | 9/1894 | Fritsche | 128/389 |
| 784,125 | 3/1905 | Sanden | 128/392 |
| 1,190,831 | 7/1916 | Werner | 128/389 |
| 3,304,708 | 2/1967 | Baehni | 128/391 |
| 3,672,352 | 6/1972 | Summers | 128/2.1 A |

OTHER PUBLICATIONS

Kubo, "IEEE Transactions on Biomedical Engineering," vol. 17, No. 2, Apr. 1970, pp. 163–166.

Primary Examiner—William E. Kamm
Attorney, Agent, or Firm—Thomas A. Fournie

[57] ABSTRACT

A therapeutic adornment or jewelry object incorporating a solar cell operable to generate a beneficial electrical current flow through the body of a person wearing same. The solar cell is mounted in a housing effective to electrically insulate the cell itself from a person's body while permitting the transmission of sunlight to the cell's active energy collecting surface. The cell has positive and negative electrical output terminals across which a voltage is generated by the energy collected. The adornment is arranged to mount the cell on a person's body with its active surface exposed to the sun and its terminals electrically connected to spaced apart points on the person's body, whereby a flow of electricity is generated through the person's body between these spaced apart body points. The adornment is illustrated in the forms of a bracelet and necklace.

12 Claims, 7 Drawing Figures

U.S. Patent  Nov. 6, 1979  Sheet 2 of 2  4,173,229
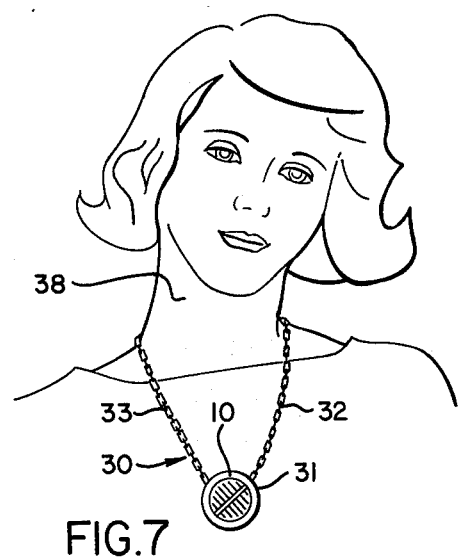
FIG.7
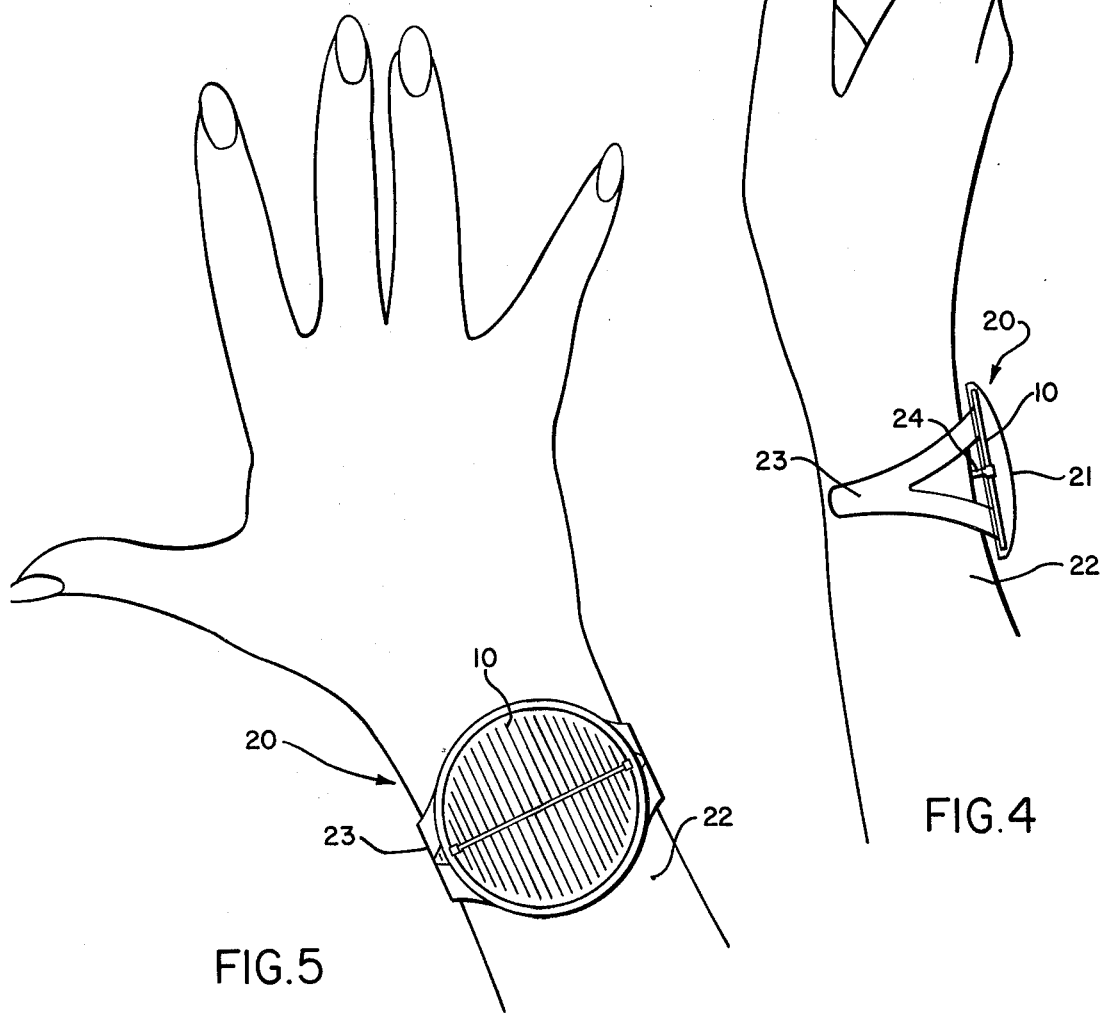
FIG.5
FIG.4

THERAPEUTIC ADORNMENTS UTILIZING SOLAR CELLS

BACKGROUND OF THE INVENTION

The present invention relates to adornments or jewelry, and more particularly to an improved and decorative therapeutic adornment or jewelry object operable to generate a beneficial flow of electrical current through the body of a person wearing same.

SUMMARY OF THE INVENTION

It is the object of the present invention to provide an improved and decorative therapeutic adornment or jewelry object operable to generate a beneficial flow of electrical current through the body of a person wearing same.

In accomplishing these and other objects, there is provided a therapeutic adornment or jewelry object incorporating a solar cell operable to generate a beneficial electrical current flow through the body of a person wearing same. The solar cell may be mounted in a housing effective to electrically insulate the cell itself from a person's body while permitting the transmission of sunlight, as well as equivalent energy rays, to the cell's active energy collecting surface. The housing is preferably transparent. The cell has positive and negative electrical output terminals across which a voltage is generated by the energy collected. The adornment is arranged to mount the cell on a person's body with its active surface exposed to the sun and its terminals electrically connected to spaced apart points on the person's body, whereby a flow of electricity is generated through the person's body between these spaced apart body points. The adornment is illustrated in the form of a bracelet and also in the form of a necklace.

Additional objects of the present invention reside in the specific construction of the embodiments of therapeutic adornments hereinafter described in conjunction with the drawings.

BRIEF DESCRIPTION OF THE DRAWINGS

FIGS. 4 and 5 illustrate the bracelet of FIG. 2 being worn on a person's arm.

FIG. 7 illustrates the necklace of FIG. 6 being worn around a person's neck.

DETAILED DESCRIPTION OF THE PREFERRED EMBODIMENTS

Figure 2:
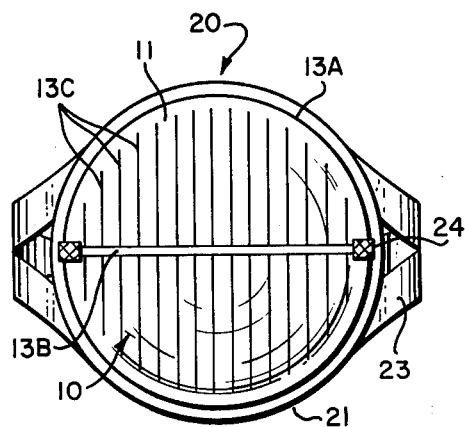
FIG. 2 is a top plan view of one such object according to the present invention, the therapeutic adornment being in the form of a bracelet.
Figure 1:
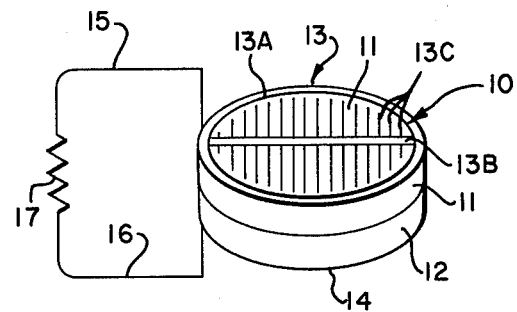
FIG. 1 is a perspective view of a solar cell for use in making therapeutic adornments or jewelry objects according to the present invention.

Referring to FIG. 1, a solar cell generally identified by the numeral 10 is there shown which is arranged for use in making therapeutic adornments or jewelry objects according to the present invention. The solar cell 10 illustrated is of a circular disc shape and further is a silicon semiconductor device made up of N type silicon 11, P type silicon 12, an N contact or electrode 13 and a P contact or electrode 14. The N electrode 13 is formed of an outer ring 13A, a diametrically extending collecting bar 13B and a plurality of energy collecting electrode elements 13C which extend in a mutually parallel disposition from the bar 13B. The P electrode 14 is formed as a circular disc which extends across the P type silicon and defines the bottom end of the solar cell 10.

In order to explain the operation of the solar cell 10, leads 15 and 16 are illustrated in FIG. 1 which connect the cell 10 across a load 17. The lead 15 is connected to N electrode 13 and the lead 16 is connected to the P electrode 14.

In the solar cell 10, the N electrode 13 is the cell's negative output terminal, the P electrode 14 is the cell's positive output terminal and the N type silicon 11 across which the energy collecting elements 13C are disposed is the cell's face or active energy collecting surface.

The cell 10 becomes a conductor and generator of electricity when its active surface 11 is exposed to sunlight, or an equivalent form of energy, containing units of energy called photons. The photons upon striking the active surface 11 of the cell 10 cause electrons to flow across the cell junction formed by the junction between the N and P type silicon 11 and 12. Thereby, negative and positive charges are generated upon the terminals 13 and 14, respectively which cause a DC voltage to be applied across the load 17 through leads 15, 16. Hence, a DC current flows through the load 17 as a result of the electrical energy generated by the solar cell 10.

In the adornments or jewelry objects hereinafter described which incorporate the solar cell 10, the load 17 through which an electrical current is caused to flow is the body of the person wearing the jewelry object.

Referring to FIGS. 2-5, a therapeutic adornment or jewelry object generally identified by the numeral 20 is there shown in the form of a bracelet. The bracelet 20 includes one of the solar cells 10. The cell 10 is mounted in a plastic transparent housing 21. The housing 21 functions to electrically insulate the cell 10 from the arm 22 of the person wearing the bracelet 20. At the same time, the housing 21 operates to transmit sunlight and equivalent energy to the solar cell 10 so that the energy may be collected by the face and active surface 11 of the cell 10.

The housing 21 illustrated is formed with a flat back 21A, convex lens shaped front surface 21B which acts a light concentrating or magnifying glass and a circular peripheral edge 21C. The disc-shaped cell 10 is encapsulated or enclosed in the housing 21 in substantially parallel disposition to the housing back surface 21A.

Figure 3:
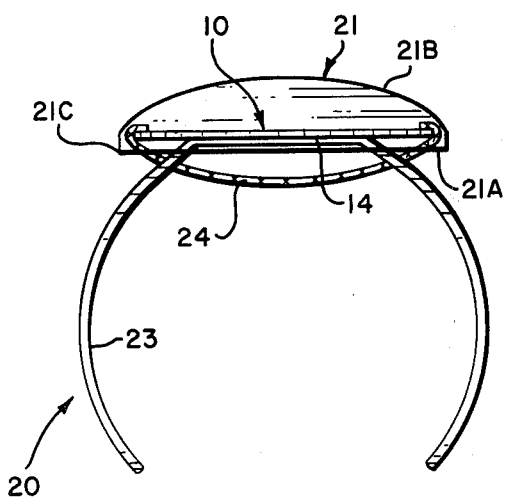
FIG. 3 is an end view of the bracelet of FIG. 2.

The arm band portion 23 of the bracelet 20 is made of an electrically conductive material and is connected as shown in FIG. 3 in electrical contact with positive electrode 14 of the solar cell 10. Connected electrically to the negative terminal 13 of the solar cell 10 is an arc shaped electrically conductive element 24. The arc shaped element 24 extends centrally and laterally across the housing back 21A and, as shown in FIG. 4, contacts and supports the bracelet 20 on the upper surface of the wrist portion of the person's arm 22.

With the bracelet 20 mounted on the person's arm 22, as shown in FIG. 4, and sunlight radiating on the top surface 21B of the cell housing 21, an electrical current is generated through the region of the person's arm 22 located between the arm band 23 and arc shaped contact element 24. Such flow of electricity through the person's arm and skin is believed to have beneficial effects.

It is noted that the voltage generated by the solar cell 10 is generally on the order of 0.5 VDC, and that the convex top surface 21 B of the energy and light transparent housing 21 is formed as a lens to enhance the collection and transmission of energy to the active surface 11 of the solar cell 10.

Figure 6:
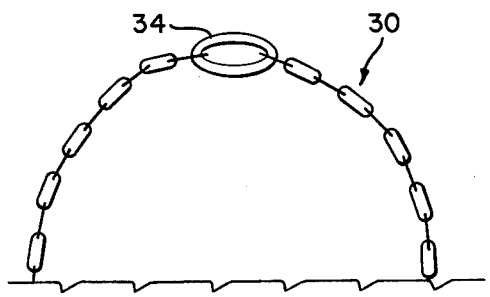
FIG. 6 is a front view of another such object according to the present invention, the therapeutic adornment being in the form of a necklace.
Figure 6:
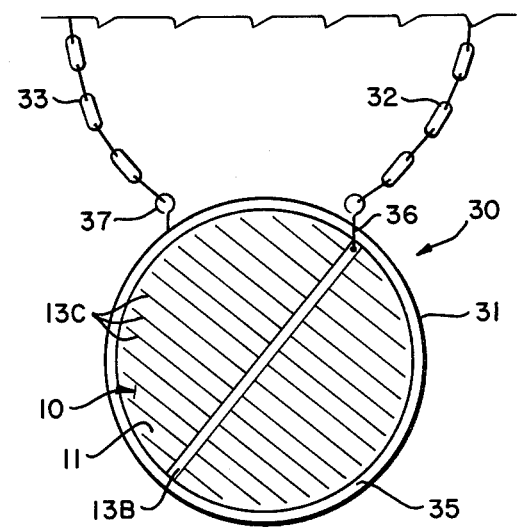

Referring now to FIGS. 6 and 7, another embodiment of therapeutic adornment or jewelry object according to the present invention is shown. This jewelry object is generally identified by the numeral 30 and is a necklace.

The necklace 30 is formed by a medallion 31, chains 32 and 33, and an interconnecting link 34. The medallion 31 is substantially flat in shape and formed by one of the solar cells 10 encapsulated or enclosed in a housing material 35. The material 35 has the characteristic of being electrically insulative and light and solar energy transmitting. Preferably, the housing is made up of a clear plastic material which may be molded around the cell 10 to enclose and encapsulate same.

The chains 32 and 33 are each electrically conductive, and are connected on one end, respectively, to the cell electrodes 13 and 14 by electrically conductive connectors 36, 37. The interconnecting link 34 mechanically joins the other ends of the chains 32 and 33 together, but is electrically nonconductive to insulate the chains 32, 33 from each other.

The necklace 30 is placed about the neck of a person 38, as shown in FIG. 7, with the cell's active surface 11 facing outwardly. With the necklace 30 so positioned on the person 38, a flow of current is generated through the person's neck from one of the chains 32, 33 to the other.

The adornment or jewelry objects above-described operate on the basis that the positive and negative terminals of the solar cells 10 incorporated therein contact the wearer's body at spaced apart body points, thereby current generated by the solar cells 10 flows through the body portion positioned between these points of contacts. It is noted that, if desired, more than one solar cell 10 could be incorporated in a jewelry object, and that such additional cells 10 could be connected electrically either in series or parallel. Further, various types of arrangements may be employed for mounting such adornment or jewelry objects on a person with the cell's active surface exposed to light and for connecting its electrodes to a wearer's body at selected spaced apart body points.

Although the invention has been herein shown and described in what is conceived to be the most practical and preferred embodiments, it is recognized that departures may be made from these specific embodiments within the scope of the invention.

I claim:

1. A therapeutic adornment in the form of a bracelet, comprising:
    solar cell means having an energy absorbing active face surface, a back surface and first and second electrical output terminals, said cell means being operable to convert sunlight and equivalent forms of energy received o its active surface into electrical energy which appears as a voltage across said output terminals;
    electrically conductive arm band means for securing said cell means on a person's limb, said arm band means being secured to said cell means to extend rearwardly therefrom around a person's limb and being electrically connected to said first output terminal; and
    electrically conductive skin contacting means secured to said cell means to extend across the back surface thereof so as to contact the skin of a person's limb underlying said cell means back surface, said skin contacting means being electrically connected to said second output terminal whereby electrical energy generated by said cell means causes a beneficial current flow through a person's limb positioned between said skin contacting means and said arm band means.

2. The invention defined in claim 1, wherein:
    said cell means is a substantially circular disk-shaped element; and
    said skin contacting means is an arc shaped member which supports said cell means on a limb of a person wearing same.

3. The invention defined in claim 2, including lens means positioned over the active face surface of said cell means for enhancing the collection and transmission of energy to the active surface of said cell means.

4. The invention defined in claim 2, including housing material enclosing said cell means, said housing material being an electrical insulative, light and solar energy transmitting materia.

5. The invention defined in claim 4, wherein said housing material is transparent plastic and the surface of said plastic material covering the active surface of said cell means has a substantially convex lens shape to act as a magnifying glass.

6. The invention defined in claim 1, including lens means positioned over the active face surface of said cell means for enhancing the collection and transmission of energy to the active surface of said cell means.

7. A therapeutic adornment in the form of a necklace, comprising:
    solar cell means having an energy absorbing active face surface, a back surface and first and second electrical output terminals, said cell means being operable to convert sunlight and equivalent forms of energy received on its active surface into electrical energy which appears as a voltage across said output terminals;
    first and second electrically conductive chains, one end of said first chain being electrically connected to said first output terminal and one end of said second chain being electrically connected to said second output terminal; and
    electrically non-conductive linking means for linking the free other ends of said chains together so as to form a necklace which can be worn around a person's neck whereby electrical energy generated by said cell means causes a beneficial current flow through the portion of a person's skin and body laying between said chains.

8. The invention defined in claim 7, wherein:
    said cell means is a substantially circular disc-shaped element; and including:
    housing material enclosing said cell means, said housing material being an electrically insulative, light and solar energy transmitting material.

9. A therapeutic adornment, comprising:
    solar cell means having an energy absorbing active face surface, a back surface and first and second electrical output terminals, said cell means being operable to convert sunlight and equivalent forms of energy received on its active surface into electrical energy which appears as a voltage across said output terminals; and cooperative first and second mounting means for securing said cell means on a person with the active surface of said cell means exposed to light, said first and second mounting means being each electrically conductive and connected to said first and second output terminals, respectively, whereby electrical energy generated by said cell means causes a beneficial current flow through the portion of a person's body positioned between said first and second mounting means.

10. The invention defined in claim 9, wherein: said cell means is a substantially circuit disc-shaped element; and including:

housing material enclosing said cell means, said housing material being an electrically insulative, light and solar energy transmitting material.

11. The invention defined in claim 10, wherein said housing material is transparent plastic and the surface of said plastic material covering the active surface of said cell means has a substantially convex lens shape to act as a magnifying glass.

12. The invention defined in claim 9, including lens means positioned over the active surface of said cell means for enhancing the collection and transmission of energy to the active surface of said cell means.

* * * * *

UNITED STATES PATENT OFFICE
CERTIFICATE OF CORRECTION

Patent No. 4,173,229　　　　　　　Dated　6 November 1979

Inventor(s)　LEON HALFON

It is certified that error appears in the above-identified patent and that said Letters Patent are hereby corrected as shown below:

In column 3, line 62, "o" should be --on--;

In column 4, line 26, "materia" should be --material--; and

In column 6, line 1, "circuit" should be --circular--.

Signed and Sealed this

First Day of April 1980

[SEAL]

Attest:

SIDNEY A. DIAMOND

Attesting Officer　　Commissioner of Patents and Trademarks